United States Patent
Seiler et al.

(10) Patent No.: US 8,454,167 B2
(45) Date of Patent: *Jun. 4, 2013

(54) PRESBYOPIA CORRECTION PROGRAM

(75) Inventors: Theo Seiler, Zurich (CH); Tobias Lorenz Florian Koller, Zurich (CH)

(73) Assignee: Wavelight AG, Erlangen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,711

(22) Filed: Mar. 28, 2011

(65) Prior Publication Data
US 2011/0190743 A1 Aug. 4, 2011

Related U.S. Application Data

(63) Continuation of application No. 12/063,976, filed as application No. PCT/EP2006/007895 on Aug. 9, 2006, now Pat. No. 7,914,149.

(30) Foreign Application Priority Data
Aug. 19, 2005 (EP) .................................. 05018062

(51) Int. Cl.
*A61B 3/00* (2006.01)
(52) U.S. Cl.
USPC .......................................... 351/246; 351/200
(58) Field of Classification Search
USPC ................................................. 351/200, 246
See application file for complete search history.

(56) References Cited

U.S. PATENT DOCUMENTS

| 5,314,422 A | 5/1994 | Nizzola |
| 5,533,997 A | 7/1996 | Ruiz |
| 6,082,856 A | 7/2000 | Dunn et al. |
| 2004/0054356 A1 | 3/2004 | Odrich et al. |
| 2004/0169820 A1 | 9/2004 | Dai et al. |
| 2004/0246440 A1 | 12/2004 | Andino et al. |
| 2006/0244906 A1* | 11/2006 | Piers et al. ............... 351/161 |
| 2006/0274261 A1 | 12/2006 | Andino et al. |

FOREIGN PATENT DOCUMENTS
WO WO 9325166 12/1993

OTHER PUBLICATIONS

International Search Report (PCT/EP2006/007895).
Bauerberg, Jorge M., MD; "Centered vs. Inferior Off-Center Ablation to Correct Hyperopia and Presbyopia;" Journal of Refractive Surgery; vol. 15; Jan./Feb. 1999; pp. 66-69.
Telandro, Alain, MD; "Pseudo-accommodative Cornea: A New Concept for Correction of Presbyopia;" Journal of Refractive Surgery; vol. 20; Sep./Oct. (suppl) 2004; pp. S714-S717.

* cited by examiner

*Primary Examiner* — Dawayne A Pinkney
(74) *Attorney, Agent, or Firm* — Haynes and Boone, LLP

(57) ABSTRACT

Systems and methods for treating presbyopia are provided. In one embodiment, a system for photorefractive treatment of presbyopia includes a laser source configured for ablating corneal tissue and a control system in communication with the laser source and configured to control the laser source to ablate conical tissue of a patient to achieve a desired corneal shape. In some instances, the control system controls the laser source by calculating a global optimum regarding curvature and asphericity of the cornea. In some instances, control system controls the laser source by calculating a central steep island and calculating a curvature and asphericity for the rest of the cornea. In some embodiments, a laser source is controlled to ablate the cornea of the patient in accordance with a calculated shape profile to achieve a desired corneal shape.

19 Claims, 4 Drawing Sheets

PRESBYOPIA CORRECTION PROGRAM

CROSS-REFERENCE TO RELATED APPLICATION

This application is a continuation of U.S. patent application Ser. No. 12/063,976 filed on Oct. 3, 2008, now U.S. Pat. No. 7,914,149, which is a United States national phase application of international patent application number PCT/EP2006/007895, filed Aug. 9, 2006, which claims priority to European Application Number 05018062.9, filed Aug. 19, 2005, each of which is hereby incorporated by reference in its entirety.

BACKGROUND

The present invention is concerned with a method of generating a computer program for control of an apparatus capable to ablate corneal tissue or a contact lens for treatment of presbyopia.

Presbyopia is the lack of capability of the eye lens to accommodate for far distance and near distance.

The prior art knows many optical approaches to presbyopia including reading glasses, monovision, multifocal contact lenses, intraocular implants, and accommodative intraocular lenses. None of these attempts can restore accommodation but all represent compromises to establish a more or less fair near vision at the costs of far vision. Some methods were designed to restore accommodation by means of scleral expansion near the ciliary body, however, have so far failed to prove efficacy.

In refractive laser surgery, first "presbyopia corrections" have been reported in the early nineties (Moreira H, Garbus J J, Fasano A, Clapham L M, Mc Donnell P J; Multiffical Corneal Topographic Changes with Excimer Laser photorefractive Keratectomy; Arch Ophthalmol 1992; 100: 994-999; Anschütz T, Laser Correction for Hyperopia and Presbyopia, Int Ophthalmol Clin 1994; 34: 105-135). However, such techniques have not gained wide clinical acceptance. More sophisticated presbyopia correction profiles have been proposed including an induced central steep island (CSI), U.S. Pat. No. 5,533,997 (Ruiz) and WO93/25166 (King, Klopotek). The present invention partially refers to the concept of CSI disclosed in the afore-mentioned patents. Also decentered steep areas have been proposed, see U.S. Pat. No. 5,314,422 to Nizzola, and Bauerberg J M, Centered vs. Inferior off-center Ablation to Correct Hyperopia and Presbyopia, J Refract Surg 1999. The prior art also suggests a near vision zone in the mid-periphery of the cornea, see Telandro A, Pseudo-accommodative Cornea: a new Concept for Correction of Presbyopia, J Refract Surg 2004; 20:S714-S717; and Cantu R, Rosales M A, Tepichin E, Curioca A, Montes V, Bonilla J; Advanced Surface Ablation for Presbyopia using the Nick EC-5000 Laser, J Refract Surg 2004, 20: S711-S713.

SUMMARY

The present invention aims at an effective method for presbyopia correction and provides a method of generating a computer program for control of a laser system for photorefractive treatment of presbyopia by ablation of tissue from or in the cornea or from a contact lens.

To this end, the method of generating a computer program for control of an apparatus for photorefractive surgery comprises the following steps:
(a) selecting an eye model,
(b) measuring the pupil diameter of the patient at far distance mesopically and at short distance photopically,
(c) selecting wanted short and far distances regarding optimum sight,
(d) calculating a global optimum regarding curvature (1/R) and asphericity (Q) of the cornea on the basis of the results obtained in steps (a) (b) and (c) by means of optical ray tracing and minimal spot diameter at the retina and
(e) deriving the computer program in accordance with the results of step (d).

This method of determining global optimum for curvature and asphericity creates a purely aspheric shape including a small amount of myopia with increased depths of focus. A stronger refractive power is obtained for near in the central area surrounded by a mid-periphery with less power. The aspheric global optimum includes an even naturally occurring corneal asphericity that provides a variable pseudoaccommodation depending on the asphericity constant Q and the pupil diameter change amplitude during the near reflex.

According to an alternative embodiment of the invention a computer program for control of an apparatus for photorefractive surgery is generated by the following steps:
(a) selecting an eye model,
(b) measuring the pupil diameter of the patient at far distance mesopically and at short distance photopically,
(c) selecting wanted short and far distances regarding optimum sight,
(d) determining a central steep island with diameter in the range of 2 to 4 millimeter and a refractive height of 1 to 4 diopters at the cornea and calculating a curvature and asphericity in the rest of the cornea depending on the central island selected, and
(e) deriving the computer program in accordance with the results of step (d).

This technique results in a multifocal cornea with two main foci. Again a stronger refractive power is obtained for near in the central area surrounded by a mid-periphery of less power. The two main driving forces for this multifocal CSI are, on the one hand, the pupil size that decreases during focusing near objects (pupillary near reflex) and, on the other hand, also the depths of focus is increased.

This CSI-configuration is a corneal analogon to the artificial bifocal, intraocular lens (IOL). Due to its increased depths of focus, the advantage of the CSI-technology is a twice better retinal image of near objects as compared to the globally optimized shape and a four times better image compared to the non-accommodated emmetropic eye.

According to a preferred embodiment of the present invention, the optimal configuration (computer program) is tested for patient satisfaction prior to surgery using contact lenses. When applying one of the two afore-mentioned ablation techniques, first contact lenses can be formed in accordance with the generated computer program and the so formed lenses are tested by the patient for a few days. Therefore the present invention also provides a method of generating a computer program product for control of an apparatus capable of ablating contact lenses.

DETAILED DESCRIPTION

Figure 1:
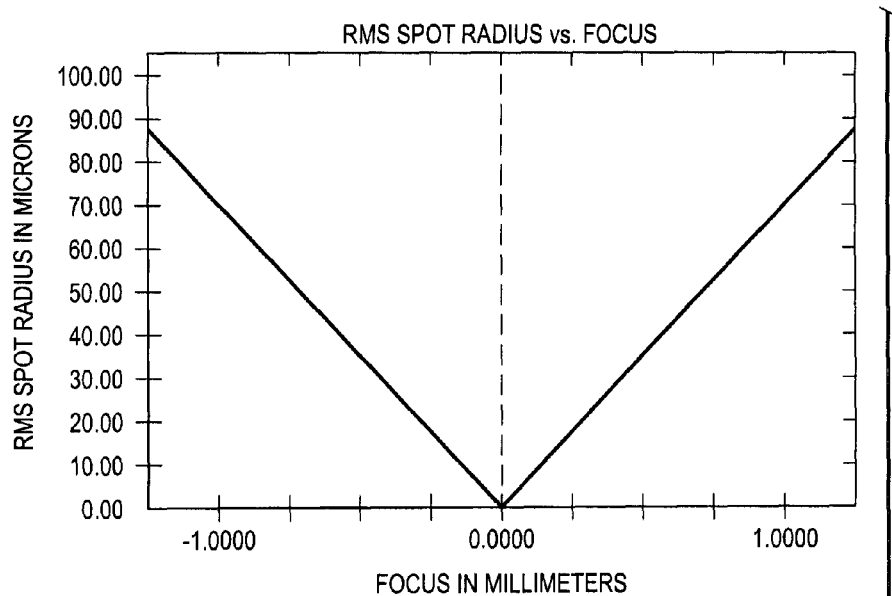
FIG. 1 is a pair of charts mapping spot diameter in the retina for far and near objects in the context of an emmetropic eye (no accommodation).
Figure 1:
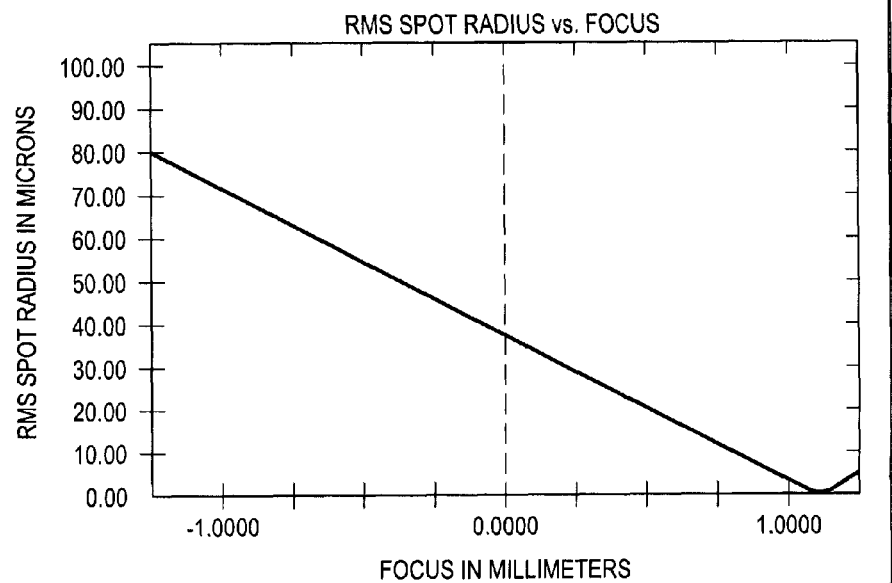

In the following the invention is described in more detail with regard to specific embodiment.

1. Theoretical Eye Model

The eye model used here is based on the model of Liou and Brennan (Liou H L, Brennan N A, Anatomically accurate, finite Model Eye for optical Modeling; J Opt Soc Am A Opt Image Sci Vis 1997; 14: 1684-1695). This model is characterized by aspheric anterior and posterior corneal and lenticular surfaces. In addition, it includes a linear refractive index gradient of $\Delta n=0.2$ inside the lens. The parameters for the emmmetropic eye are listed in Table 1. The anterior cornea was approximated by a biconoid surface $$z=(x^2/R_x+y^2/R_y)/(1+(1-(1+Q_x)x^2/R_x^2-(1+Q_y)y^2/R_y^2)^{1/2}) \quad 1.$$

where $1/R_{x,y}$ are the curvatures and $Q_{x,y}$ are the asphericity constants in the corresponding main meridians, the positive z-direction points into the eye, the positive y-direction upwards. The reference wavelength is 555 nm. In order to include the Stiles-Crawford effect a transmission filter is introduced (Moon P, Spencer D E, On the Stiles-Crawford Effect, J Opt Soc Am 1944; 34: 319-32)

$$T(r)=\exp(-ar^2) \quad 2.$$

with the apodization constant $a=0.105$ and r the radial distance from the center of the pupil.

To model central or decentered steep islands, cubic spline functions are introduced with steps of 0.5 mm radial distance from the apex of the cornea. All optical surfaces are centered on the optical axis. A pupil diameter of 5 mm is used for simulation of the far distant (object distance 5 m) and 2.5 mm for near (object distance 0.4 m) vision configuration. The object is a point light source located 1° up. Additional (reading) glasses have a distance of 12 mm from the vertex of the cornea.

The quality of the retinal image is described either by the "rms spot diameter" or the "rms wavefront error" similar to the technique published earlier (Seiler, T Reckmann W, Maloney R K, Effective spherical Aberration of the Cornea as a quantitative Descriptor of the Cornea, J Cataract Refract Surg. 1993; 19 Suppl: 155-65).

All calculations can be performed with a commercially available optical design program such as, e.g., the optical design program ZEMAX EE, version March 2004 (Zemax Development Cooperation, San Diego, Calif.). Useful is an optimization process aiming on a minimal spot diameter in the retina (circle of least confusion), but depending on the problem also modulation transfer function, wavefront error and point spread function can be used as optimization operands.

The quality of the retinal image is determined in near and far distant configuration for the following scenaria (Table 2): (1) the emmetropic eye optimized regarding asphericity and eye length, (2) the global optimum for simultaneous near and far distant vision optimized regarding R and Q, (3) central steep island with a diameter of 3 mm and a refractive height of 3 D optimized regarding R and Q, (4) scenario (3) but the central steep island is decentered towards inferior in 0.5 mm-steps up to 3 mm.

2. Results

Optimization of eye length and asphericity in the emmetropic eye for far distance vision yielded approximately physiologic values (Table 1): an eye length of 24.01 mm and a corneal asphericity constant of $-0.158$. The minimal spot diameter in the retina $d=1.396$ microns as well as the wavefront error of 0.034 waves are close to the diffraction limit. Introducing a corneal astigmatism of 0.75 D increases the minimal spot diameter to 29.662 microns and the wavefront error to 1.338 waves, a value that is clinically observed.

Comparing the spot diameter in the retina for the far and near distant object reveals in the emmetropic eye (no accommodation) a shift of the focus of 890 microns behind the retina (FIG. 1) which can be shifted back into the retina by a reading glass of 2.32 diopters with a vertex distance of 12 mm.

Figure 2:
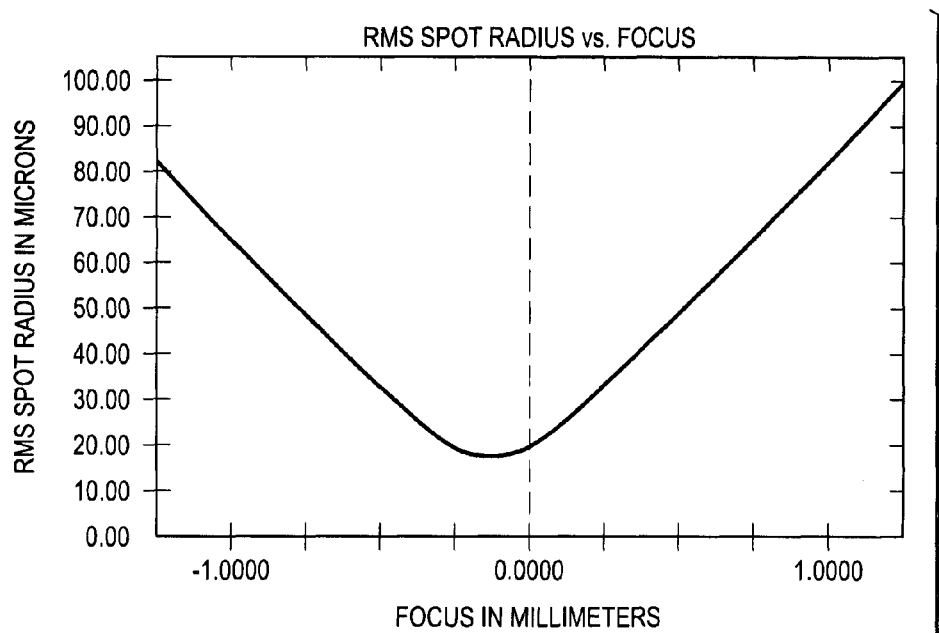
FIG. 2 is a pair of charts mapping spot diameter in the retina for far and near objects in the context of a global optimum.
Figure 2:
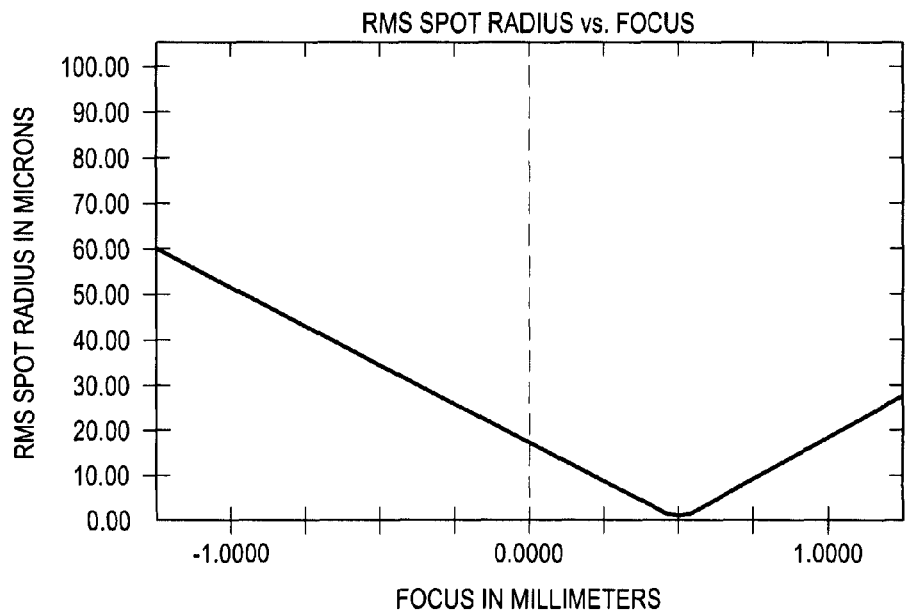

FIG. 2 demonstrates the spot diameter through the retina for the global optimum regarding R and Q (GO) in the far and near object configuration. It is worth mentioning that the two configurations differ not only by the distance of the object but also by the pupil diameter. The spot diameter in the retina increases to 37.61 microns for the far distant object and decreases to 34.22 microns for the near object (Table 2). Comparing the optimized emmetropic eye (scenario 1) with the global optimum (scenario 2) the difference in a case of a CSI with 3 mm in diameter and 3 diopters in height consists in an increase in central corneal power of 1.4 diopters (myopia) and a more prolate corneal shape $Q_{GO}=-0.68$. Again, by using a reading glass of 1.01 diopters the focus can be shifted into the retina yielding a spot diameter of 3.56 microns. The other CSI configurations yield different values for curvature $1/R$ and asphericity constant Q.

Figure 3:
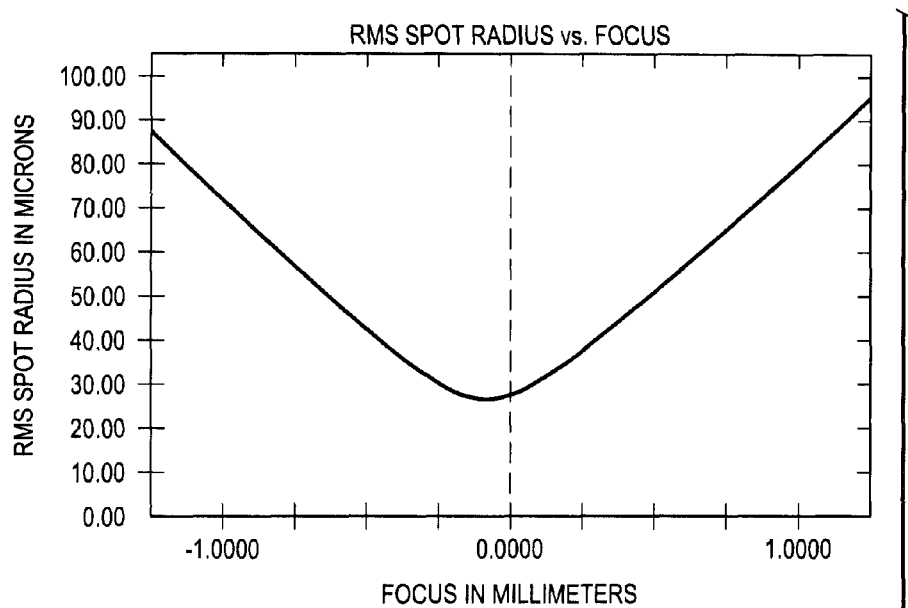
FIG. 3 is a pair of charts mapping spot diameter in the retina for far and near objects in the context of a central steep island.
Figure 3:
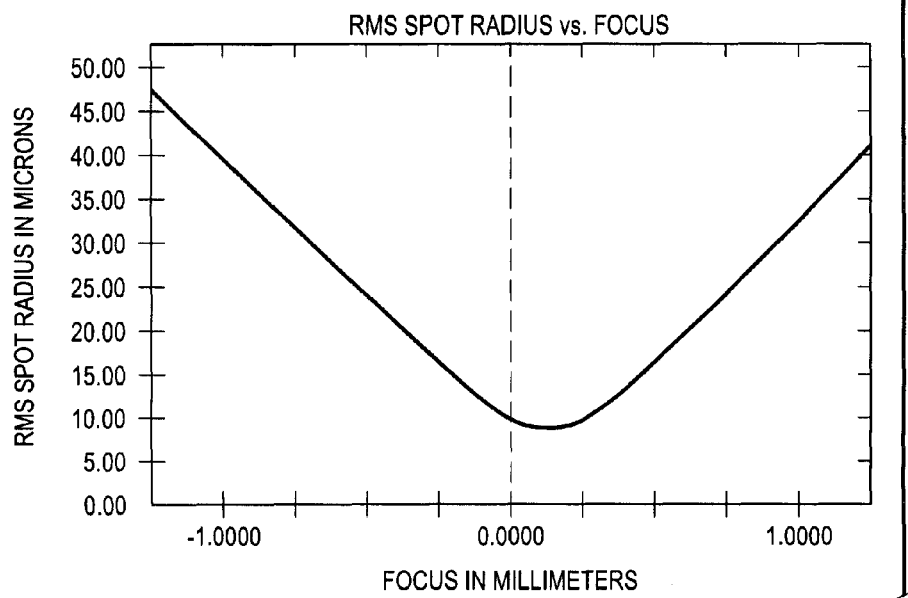

The spot diameter through the retina for the central steep island with optimized R and Q for simultaneous far and near vision is depicted in FIG. 3. Whereas for the far distant object the spot diameter is comparable to that in the global optimum (GO) it is better by a factor of approximately 2 for near vision. However, reading glasses cannot improve this result any more.

Figure 4:
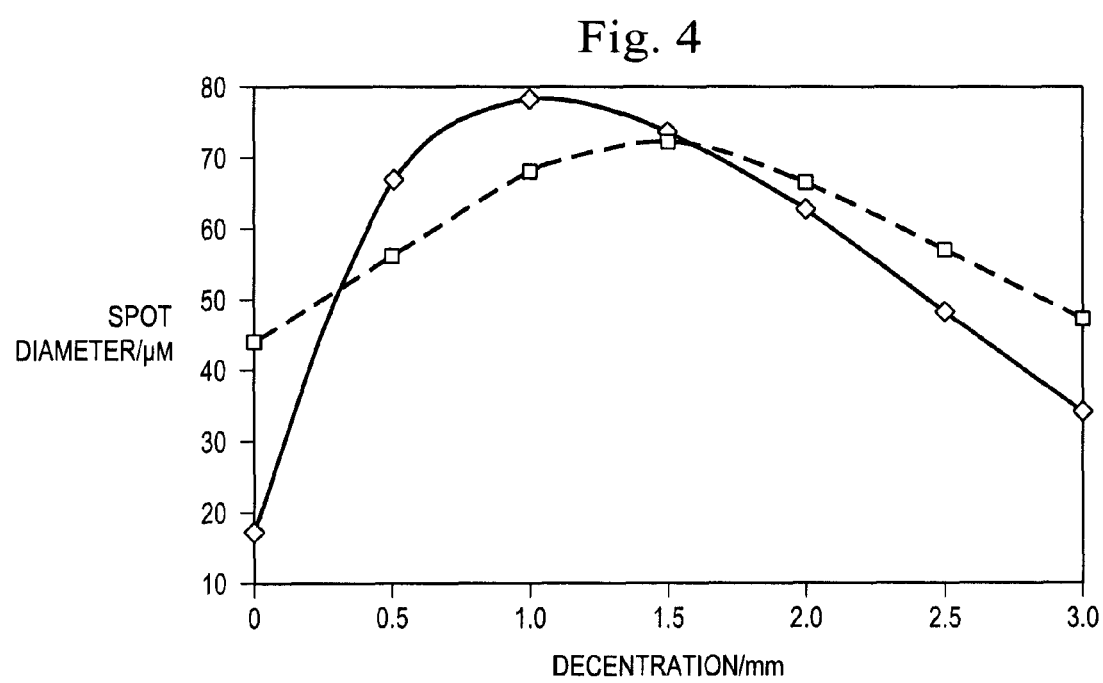
FIG. 4 is a graph mapping spot diameter in the retina between a central steep island and an off-center steep island.

Decentration of the steep island degrades the quality of the retinal image which is shown in FIG. 4. Compared to the central steep island a decentration of for example 1 mm results in a 1.6-fold worsening for far and 4.7-fold worsening for near vision. Again, reading glasses can only marginally improve near vision.

3. Discussion

The major finding of this study is that there are configurations of the corneal shape that represent a clinically meaningful compromise of minor losses in far distance vision with improvement of near vision. The two most attractive approaches are (1) the central steep island combined with appropriate curvature and asphericity in the rest of the cornea and (2) the global optimum for curvature and asphericity. Whereas the first proposal means a multifocal cornea with two main foci, the second one is a purely aspheric shape creating a small amount of myopia with increased depth of focus. Both corneal shapes provide a stonger refractive power for near in the central area surrounded by a mid-periphery with less power. The two main driving forces of the multifocal CSI- as well as the aspheric GO-shape are, on one hand, the pupil size that decreases during focusing near objects (pupillary near reflex) and, on the other hand, also the depth of focus is increased in both optical scenaria.

The CSI-configuration is a corneal analogon to the artificial bifocal IOL (Jacobi K W, Nowak M R, Strobel J, Special Intraocular Lenses, Fortschr Ophthalmol 1990; 87: S29-S32) with all its known advantages and disadvantages such as loss in contrast sensitivity, halos, glare, and reduced visual satisfaction (Leyland M D, Langan L, Goolfee F, Lee N, Bloom P A, Prospective Randomized Double-Masked Trial of Bilateral Multifocal, Bifocal or Monofocal Intraocular Lenses, Eye 2002; 16: 481-490); (Pieh S, Lackner B, Hanselmayer G, Zohrer R, et al., Halo Size under Distance and Near Conditions in Refractive Multifocal Intraocular Lenses, Br J. Ophthalmol. 2001; 85: 816-821); (Lesueur L, Gajan B, Nardin M, Chapotot E, Arne J L, Comparison of visual Results and Quality of Vision between Two Multifocal Intraocular Lenses. Multifocal Silicone and Bifocal PMMA, J Fr Ophthalmol, 2000; 23: 355-359); (Knorz M C, Seiberth V, Ruf M, Lorger C V, Liesenhoff H, Contrast Sensitivity with monofocal and biofocal Intraocular Lenses, Ophthalmologica 1996; 210: 155-159); (Haaskjold E, Allen E D, Burton R L, et al., Contrast Sensivity after Implantation of Diffractive Bifocal and Monofocal Intraocular Lenses, J Cataract Refract Surg 1998; 24: 653-658).

In contrast, the aspheric GO includes an even naturally occurring corneal asphericity that provides a variable pseudoaccomodation depending on the asphericity constant Q and the pupil diameter change amplitude during the near reflex.

Due to its increased depth of focus the advantage of the CSI is a twice better retinal image of near objects compared to the GO-shape and four times better compared to the non-accommodated emmetropic eye, but also due to the increased depth of focus one of its disadvantages is the inability to improve both near and far vision by means of spectacles. In addition, the effect of the CSI is critically dependent on centration: already at a decentration of 0.1 mm the advantage of the CSI compared with GO is gone and a degradation of the retinal image for distance vision by a factor of 1.3 happens. Using modern eye-trackers centration is achieved reliably, however, there is a principal problem because the CSI should be centered regarding the visual axis and the crossing point of the visual axis through the cornea is uncertain and hard to determine. Reasonable centration is much easier obtained using the GO-approach because it does not contain such a localized optical inhomogeneity.

A major disadvantage of a multifocal optics of the eye is the loss in mesopic vision as measured in low contrast visual acuity and contrast sensitivity that has been repeatedly reported after multifocal intraocular implants satisfaction (Leyland M D, Langan L, Goolfee F, Lee N, Bloom P A, Prospective randomized double-masked Trial of Bilateral Multifocal, Bifocal or Monofocal Intraocular Lenses, Eye 2002; 16: 481-490); (Lesueur L, Gajan B, Nardin M, Chapotot E, Arne J L, Comparison of visual Results and Quality of Vision between Two Multifocal Intraocular Lenses. Multifocal Silicone and Bifocal PMMA, J Fr Ophthalmol. 2000; 23: 355-359); (Knorz M C, Seiberth V, Ruf M, Lorger C V, Liesenhoff H, Contrast Sensitivity with monofocal and biofocal Intraocular Lenses, Ophthalmologica 1996; 210: 155-159); (Haaskjold E, Allen E D, Burton R L, et al., Contrast Sensivity after Implantation of Diffractive bifocal and monofocal Intraocular Lenses, J Cataract Refract Surg 1998; 24: 653-658).

Many patients complain about an increase of halos (Pieh S, Lackner B, Hanselmayer G, Zohrer R, et al., Halo Size under distance and near Conditions in Refractive Multifocal Intraocular Lenses, Br J. Ophthalmol. 2001; 85: 816-821). Regarding these optical side effects we would like to cite a recent statement of Georges Baikoff (Baikoff G, Matach G, Fontaine A, Ferraz C, Spera C, Correction of Presbyopia with refractive multifocal Phakic Intraocular Lenses, J Cataract Refract Surg. 2004; 30: 1454-1460): "Optical defects are inevitable with multifocal IOLs; . . . ". Although this argument holds mainly for the clearly multifocal CSI-shape of the cornea a similar loss in contrast sensitivity is expected to occur also with strongly aspheric corneas. However, an asphericity constant Q of −0.7 as intended in the global optimum (GO) is only −0.5 away from the average (Kiely P M, Smith G, Carney L G, The Mean Shape of the human Cornea, Optica Acta 1982; 29: 1027-1040) and compares favorably with the up to three times larger changes in the asphericity constant after standard myopic LASIK of up to +1.5 (Holladay J T, Dudeja D R, Chang J. Functional Vision and conical Changes after Laser in Situ Keratomileusis determined by Contrast Sensitivity, Glare Testing, and Corneal Topography. J Cataract Refract Surg. 1999; 25: 663-669); (Koller T, Iseli H P, Hafezi F, Mrochen M, Seiler T, Q-Factor customized Ablation Profile for the Correction of Myopic Astigmatism, J Cataract Refract Surg. (2005 submitted). Also, emmetropic or hyperopic eyes receiving a hyperopia correction for attempted slight myopia for monovision experience a shift in asphericity towards prolate that is in the order of −0.5 (Chen C C, Izadshenas A, Rana M A, Azar D T, Conical Asphericity after hyperotic Laser in Situ Keratomileusis. J Cataract Refract Surg, 2002; 28: 1539-1545).

The currently most frequently used concept of presbyopia correction is the monovision approach where the dominant eye is corrected for emmetropia and the non-dominant for minor myopia ranging from −0.5 D to −2.0 D (Miranda D, Krueger R R, Monovision Laser in Situ Keratomileusis for pre-presbyopic and prescbiopic Patients, J Refract Surg. 2004; 20: 325-328); (Mc Donnell P J, Lee P, Spritzer K, Lindblad A S, Hays R D, Assiocations of Presbyopia with vision-targeted health-related Quality of Life, Arch Ophthalmol. 2003; 121: 1577-1581); (Johannsdottir K R, Stelmach L B, Monovision: A Review of the scientific Literature, Optom Vis Sci. 2001; 78: 646-651); Greenbaum S, Monovision Pseudophakia, J Cataract Refract Surg. 2002; 28: 1439-1443); (Jain S, Ou R, Azar D T, Monovision Outcomes in presbyopic Individuals after refractive Surgery, Ophtalmology. 2001; 108: 1430-1433). In clinical surgery practice the optimal configuration is tested for patient satisfaction prior to surgery using contact lenses. A similar strategy may be appropriate when applying one of the two presented ablation profiles including binocular versus monocular multifocal/aspheric treatment. Assuming that in the future we will have access to such a set of contacts and the patient may decide for surgery after a few days of simulation of his future optics we are still at risk of dissatisfaction. In a study testing monovision in presbyopic patients by means of contact lenses the immediate response was nota good predictor for satisfaction after two weeks (Du Toit R, Ferreira J T, Nel Z J, Visual and nonvisual Variables implicated in Monovision Wear, Optom Vis Sci. 1998; 75: 119-125).

To facilitate understanding the correlation of minimal spot diameter and visual acuity the spot diameters in the retina for various degrees of low myopia are considered. With a myopia of −0.5 diopters an uncorrected vision of approximately 20/30 may be obtained under scotopic lightning conditions which corresponds to a spot diameter in the retina of 40 microns. This may serve as a gross reference for the two configurations CSI and GO. With CSI a near visual acuity of 20/25 and a far distant VA of 20/30 seems to be obtainable, good lightning conditions and appropriate pupil diameters provided. With the GO approach both near and far VA arc at approximately 20/30 with the option to improve near VA to 20/20 with reading glasses, an option that we do not have in CSI-treated eyes. It is clear that only prospective controlled studies will give us better information about the visual acuities achieved after presbyopia corrections.

The last and most critical point that needs to be discussed is that any presbyopia "correction" necessarily is a kind of compromise. Whatever one wins in the near domain must be lost in far distance vision and vice versa. Having this in mind and considering the dependence of the optical result on pupil sizes under various conditions and its centration it is obvious that any ablative presbyopic correction should be handled as a customized treatment and simulated preoperatively by means of contact lenses. One of the strongest predictors of a satisfying outcome of refractive surgery is the patient's expectation. Especially with presbyopia correction the balance of the optically possible and the individually desirable has to be made preoperatively. Also important in this context is the reversibility of the operation: simple monovision and GO is easy to correct by means of a reoperation, whereas the CSI profile is more difficult to reverse although recently progress has been reported using advanced customized ablation by means of Zernike and Fourier algorithms (Hafezi F, Iseli H P, Mrochen M, Wüllner C, Seiler T, A New Ablation Algorithm for the Treatment of Central Steep Islands after Refractive Laser Surgery, J Cataract Refract Surg. (2005 submitted).

4. The Method

Resulting from the above findings, the present invention proposes the following method:

The shape of the cornea, represented by its curvature (1/R), the asphericity (Q) and a central steep island (CSI) are formed individually (i.e. for a particular patient) such that the optical quality (sharpness) of the image at the retina is optimal simultaneously at the following two configurations: (a) far object (e.g. the distance to the eye is 5 m or more), the pupil diameter is large (e.g. 5 mm, generally speaking larger than 3.5 or 4 mm) and (b) near object (e.g. the object is 0.4 m from the eye, generally speaking nearer than 0.6 m), the pupil diameter is small (e.g. smaller than 3 mm).

Such an individually adapted configuration can be simulated by contact lenses used by the patient. This includes the option of monovision, e.g. the dominant eye for far sight and the non-dominant eye for presbyopia correction.

The method can be summarized as follows:

(1) Measuring the pupil diameter for a far distance mesopically and a short distance photopically, (2) Defining the distances with intended optimum sight for far distance and near distance, (3) Calculating the global optimum for R and Q by means of optical designer software (for example ZEMAX) on the basis of a selected eye model (e.g. Liou-Brannen), using, optionally, the refinement disclosed in (Seiler T, Reckmann W, Maloney R K, Effective spherical Aberration of the Cornea as a quantitative Descriptor of the Cornea, J Cataract Refract Surg. 1993; 19 Suppl: 155-65). This may or may not include a CSI, (4) Manufacturing a corresponding contact lens (if not available on stock) that is stabilised on the eye regarding the optical axis, (5) If the patient is satisfied with the result the cornea can be treated accordingly.

The CSI typically has a diameter of 3 mm at the cornea (the range is 2 to 4 millimetre) and a refractive power of 3 dpt (a range of 2 to 4 dpt). The parameters are entered into the above-stated software by means of cubic spline functions, for example.

For an average eye (R=7.77 mm Q=−0.15) a myopia, without CSI, of −1.5 dpt and Q-factor of −0.7 is obtained. Including CSI a small hyperopia of +0.9 dpt and a Q-value of +0.22 should be aimed at.

When determining the global optimum the wanted configurations for near and far are defined (distances, pupil diameters) and the starting values of R and Q (where required including astigmatism) are entered into the program. Thereafter, two runs for optimization are started (one including CSI, the other without CSI). The values of R and Q are entered as operands which are freely variable and the program is iteratively run until the quality of the picture at the retina, defined by the minimum spot radius at the retina or the MTF (Modulation Transfer Function) or the point spread function is optimized. The such optimized optical configuration of the cornea is aimed at when ablating the cornea or the lens respectively.

TABLE 1

Parameters of the optimized emmetropic eye model

| Surface | curvature radius R (mm) | asphericity Q | apex position (mm) | refractive index |
|---|---|---|---|---|
| ant. cornea | 7.77 | −0.158 | 0.00 | 1.376 |
| post. cornea | 6.4 | −0.6 | 0.52 | 1.336 |
| pupil | 13.0 | 0 | 3.68 | 1.336 |
| ant. lens | 12.4 | −0.94 | 3.68 | 1.453* |
| post. lens | −8.1 | −0.96 | 7.70 | 1.336 |
| retina | 12.0 | 0 | 24.01 | — |

*The lens includes a linear gradient of refractive index increasing from 1,453 at the surfaces to 1,652 in the center

TABLE 2

Quality of the retinal image (point light source, λ = 550 nm)

| optical scenario | minimal spot diameter (microns) | |
|---|---|---|
| | far distance (5 m) | near distance (0.4 m) |
| 1. emmetropic eye optimized (Q = −0.158) | 1.40 | 65.48 |
| 2. corneal astigmatism 0.75D (Q = −0.158). | 29.66 | 76.85 |
| 3. global optimum for R and Q (R = 7.55; Q = −0.68) | 37.61 | 34.22 |
| 4. central steep island optimized R and Q (R = 7.92; Q = +0.22) | 44.47 | 17.62 |
| 5. decentered steep island, decentered by 1 mm, optimized R and Q (R = 7.68; Q = −0.42) | 68.84 | 82.85 |
| 6. centered steep annulus optimized R and Q (R = 7.21; Q = −1.72) | 130.1 | 77.62 |

What is claimed is:

1. A system for photorefractive treatment of presbyopia, the system comprising:
    a laser source configured for ablating corneal tissue;
    a control system in communication with the laser source, the control system configured to control the laser source to ablate corneal tissue of a patient to achieve a desired corneal shape, wherein the control system determines the manner in which to control the laser source to achieve the desired corneal shape by calculating a global optimum regarding curvature and asphericity of the cornea based on a selected eye model, a pupil diameter of the patient measured at a far distance mesopically, a pupil diameter of the patient measured at a short distance photopically, a desired far distance for optimum sight, and a desired near distance for optimum sight.

2. The system of claim 1, wherein the selected eye model is selected from a plurality of available eye models.

3. The system of claim 1, wherein the selected eye model is a Liou-Brennan model.

4. The system of claim 1, wherein the desired far distance for optimum sight is 5 m or more.

5. The system of claim 4, wherein the desired near distance for optimum sight is 0.6 m or less.

6. The system of claim 1, wherein the calculated asphericity is constant across the cornea.

7. The system of claim 1, wherein the global optimum regarding curvature is calculated such that the optical quality of an image at the retina is optimized for both far and near distance objects, wherein a far distance object is 5 m or more from the eye and a near distance object is 0.6 m or less from the eye.

8. The system of claim 7, wherein the global optimum regarding curvature is calculated such that for far distance objects the eye has pupil diameter of 3 mm or greater and for near distance objects the eye has a pupil diameter of 3 mm or less.

9. The system of claim 8, wherein the global optimum regarding curvature is calculated such that for far distance objects the eye has pupil diameter of 5 mm or greater.

10. The system of claim 1, wherein the global optimum and asphericity are calculated using optical ray tracing and minimal spot diameter at the retina.

11. A method for photorefractive treatment of presbyopia, the method comprising:
    measuring a pupil diameter of a patient at a far distance mesopically;
    measuring a pupil diameter of the patient at a near distance photopically;
    selecting a desired far distance for optimum sight;
    selecting a desired near distance for optimum sight;
    calculating a global optimum regarding curvature and asphericity of a cornea of the patient based on the mesopically measured pupil diameter of the patient, the photopically measured pupil diameter of the patient, the selected desired far distance, and the selected desired near distance; and
    controlling a laser source to ablate the cornea of the patient in accordance with the calculated global optimum to achieve a desired corneal shape.

12. The method of claim 11, further comprising:
    obtaining a contact lens corresponding to the calculated global optimum for application to the patient.

13. The method of claim 11, wherein the selected desired far distance for optimum sight is 5 m or more.

14. The method of claim 13, wherein the selected desired near distance for optimum sight is 0.6 m or less.

15. The method of claim 11, wherein the calculated asphericity is constant across the cornea.

16. The method of claim 11, wherein the global optimum regarding curvature is calculated such that the optical quality of an image at the retina is optimized for both far and near distance objects, wherein a far distance object is 5 m or more from the eye and a near distance object is 0.6 m or less from the eye.

17. The method of claim 11, wherein the global optimum regarding curvature is calculated such that for far distance objects the eye has pupil diameter of 3 mm or greater and for near distance objects the eye has a pupil diameter of 3 mm or less.

18. The method of claim 17, wherein the global optimum regarding curvature is calculated such that for far distance objects the eye has pupil diameter of 5 mm or greater.

19. The system of claim 11, wherein the global optimum regarding curvature and asphericity are calculated using optical ray tracing and minimal spot diameter at the retina.

\* \* \* \* \*